United States Patent [19]

Fujii et al.

[11] Patent Number: 5,672,489

[45] Date of Patent: Sep. 30, 1997

[54] CATALYTIC ANTIBODIES HYDROLYZING ACYLATED CARBOHYDRATES IN A REGIOSELECTIVE AND STEREOSELECTIVE MANNER

[75] Inventors: Ikuo Fujii; Yoshiharu Iwabuchi, both of Suita; Hideaki Miyashita, Habikino, all of Japan

[73] Assignee: Protein Engineering Research Institute, Osaka, Japan

[21] Appl. No.: 602,595

[22] Filed: Feb. 16, 1996

Related U.S. Application Data

[63] Continuation of Ser. No. 209,622, Mar. 14, 1994, abandoned.

[30] Foreign Application Priority Data

Sep. 8, 1993 [JP] Japan ................... 5-223231

[51] Int. Cl.$^6$ .......................... C12P 19/00; C12N 9/00
[52] U.S. Cl. ................. 435/72; 435/74; 435/188.5
[58] Field of Search ..................... 435/188.5, 72, 435/74

[56] References Cited

U.S. PATENT DOCUMENTS

| | | | |
|---|---|---|---|
| 4,888,281 | 12/1989 | Schochetman et al. | 435/72 |
| 5,030,717 | 7/1991 | Tramontano et al. | 530/387 |
| 5,190,865 | 3/1993 | Schultz | 435/108 |
| 5,250,426 | 10/1993 | Lerner et al. | 435/146 |
| 5,298,409 | 3/1994 | Schultz | 435/106 |

OTHER PUBLICATIONS

Haines, A.H. (1981) Adv. Carbo. Chem and Biochem. 39, 13–70.
Fujii, I., et al. (1991) J. Am. Chem. Soc. 113, 8528–8529.
Pollack, S. J. et al. (1986) Science 234, 1570–1573.
Benkovie, S. J., (1992) Ann. Rev. Biochem. 61, 29–54.
Tramontano, A., et al. (1986) Science 234, 1566–1570.

*Primary Examiner*—Charles L. Patterson, Jr.
*Attorney, Agent, or Firm*—Wenderoth, Lind & Ponack

[57] ABSTRACT

A method of regio-and stereoselective hydrolysis to deprotect an acylated hydroxy group in acylated carbohydrates, which contributes to synthesis of complex oligosaccharides, is provided. The method utilizes catalytic antibodies as hydrolase.

17 Claims, 1 Drawing Sheet

CATALYTIC ANTIBODIES HYDROLYZING ACYLATED CARBOHYDRATES IN A REGIOSELECTIVE AND STEREOSELECTIVE MANNER

This application is a continuation of now abandoned application, Ser. No. 08/209,622, filed Mar. 14, 1994, now abandoned.

This invention relates to a simple synthetic method for complex oligosaccharides. In general, it relates to a method of regioselective and stereoselective hydrolysis by catalytic antibodies. In particular, it relates to a method of regioselective and stereoselective hydrolysis to deprotect acylated carbohydrates, including monosaccharides and oligosaccharides, in which hydroxy groups are protected by the same acyl group. The invention contributes not only to basic research for elucidation of biological function of oligosaccharides but also development of useful oligosaccharide drugs.

It is gradually becoming clear that (a) glycolipids on cell-surfaces and oligosaccharides of glycoproteins alter through development and canceration of cells, (b) oligosaccharides of glycoproteins function as a receptor of virus and toxin, and (c) oligosaccharides of glycoproteins are associated with cell-cell interactions. According to the recognition of biological importance of oligosaccharides of glycoproteins, research of chemical synthesis of them has become more intensive.

In general, oligosaccharides are synthesized by sequential glycosylation of monosaccharides. There are two major problems of synthesizing oligosaccharides. One is to control stereochemistry of glycosylation. The other is to control linkage positions in the formed oligosaccharides, which is very important, because there are many hydroxy groups in oligosaccharides. It is necessary to differentiate a desired hydroxy group for glycosylation. In synthesis of complex oligosaccharides, a desired hydroxy group at the non-reducing end of the extending oligosaccharides is selectively deprotected and is subjected to glycosylation with an added monosaccharide. To date, protected carbohydrates, in which the hydroxy group is used for the next glycosyl linkage is protected with ester, ether, ketal, and carbonate that can be selectively removed, are synthesized and used for coupling with non-reducing end of oligosaocharides. However, syntheses of such selectively protected carbohydrates require complicated combinations of varieties of protecting groups for chemically competing hydroxy groups. Thus, the synthesis procedure requires many steps consuming time and effort.

Recently, the methods for introducing catalytic activity into antibodies have been developed (A. Tramontano, K. D. Janda, R. A. Lerner, Science, 234, 1566 (1986)). These catalytic antibodies have potential to be useful bio-catalysts for selective chemical transformations. Therefore, the inventors invent catalytic antibodies, which remove multi-stepped procedures for synthesis of selective-protected carbohydrates and simplify synthesis of oligosaccharides. If such catalytic antibodies could decrease the effort to protect and deprotect hydroxy groups in carbohydrates, biologically important oligosaccharides will be easily available. From the point of view mentioned above, the inventors have developed the first catalytic antibodies which deprotect acylated carbohydrates in a regioselective and stereoselective manner.

The present invention is directed to a method of regio- and stereoselective hydrolysis to deprotect an acylated hydroxy group in carbohydrates, which is characterized in that the hydrolysis is achieved by using catalytic antibodies. The method is applicable both to monosaccharides and oligosaccharides. The method can be achieved by two steps as follows:

(a) preparation of protected carbohydrates by acylation of all hydroxy groups in a monosaccharide with a given carboxyl compound, and (b) deacylation of a single protected hydroxy group in the monosaccharide, regioselectively and stereoselectively by catalytic antibodies, or (a) preparation of protected carbohydrates by acylation of all hydroxy groups in an oligosaccharide with a given carboxyl compound, and (b) deacylation of a single protected hydroxy group at the non-reducing end of the monosaccharide in a regioselective and stereoselective manner by using catalytic antibodies.

In the chemical transformation of monosaccharides, a primary hydroxy group at the C-6 position is easily differentiated from other hydroxy groups, because of its higher reactivity. On the other hand, the hydroxy groups at C-3 and C-4 positons have identical chemical reactivity. Accordingly, it is very difficult to conduct different chemical reactions between the hydroxy groups at C-3 and C-4 positions. Thus, the object of the present invention is to establish a method which permits selective or exclusive reaction on only one of C-3 and C-4 positions. Thus, one object of the present invention is to provide catalytic antibodies that selectively hydrolyze the ester bond at C-4 position in the acetylglucosamine acylated at C-3 and C-4 positions as shown below, and another object of the invention is to provide a method for conducting such selective hydrolysis by the use of such catalytic antibodies.

Reaction Scheme 1

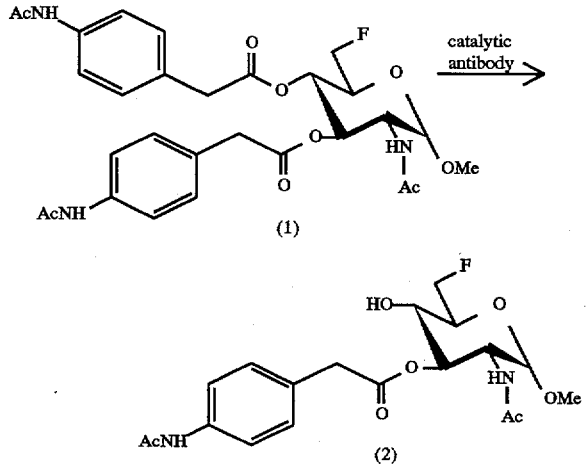

The antibodies of the invention are produced by immunizing an animal with a phosphonate (3) shown below, which works as a hapten, and which is thought to be a transition state analog of ester hydrolysis.

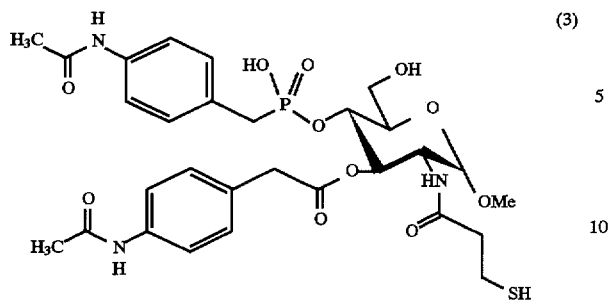
(3)
The phosphonate(3) can be synthesized in procedures shown in Reaction Scheme 2.
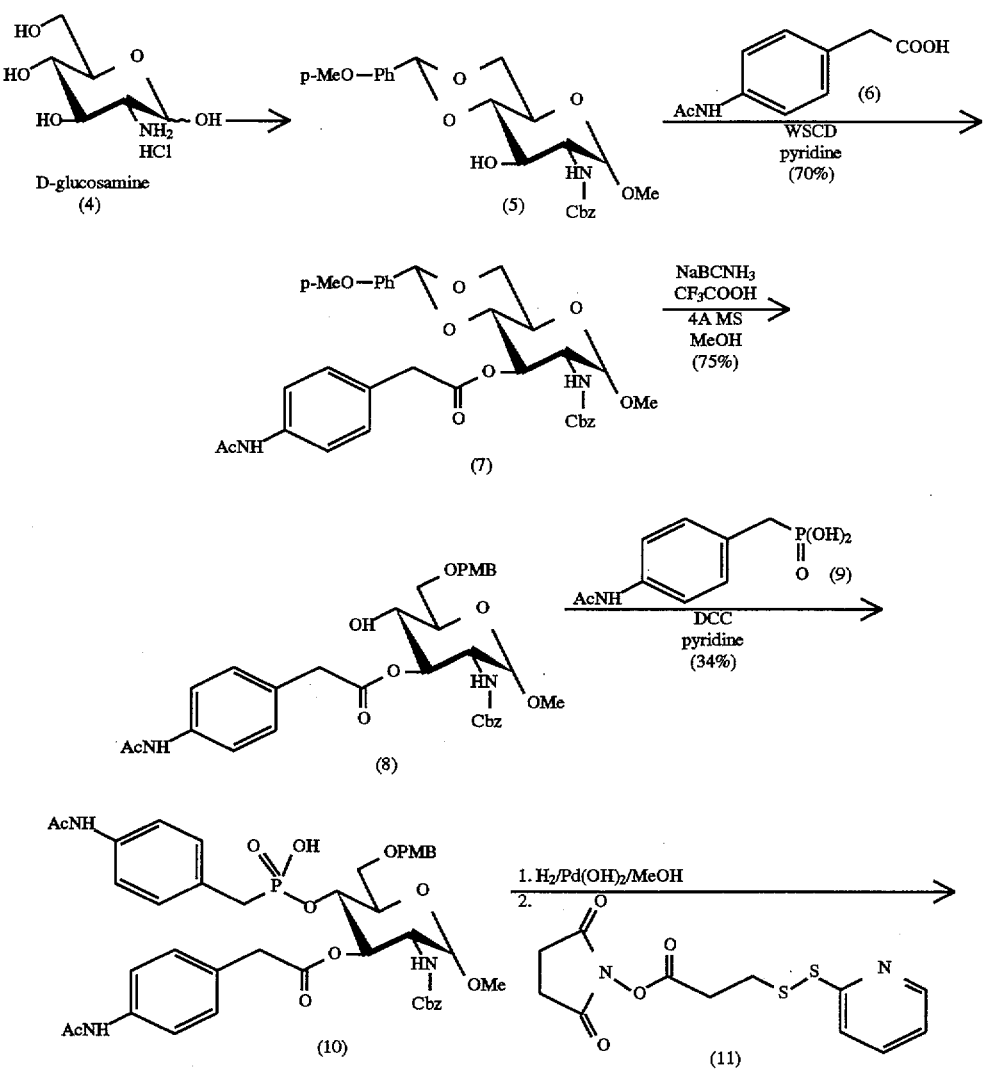

-continued
Reaction Scheme 2

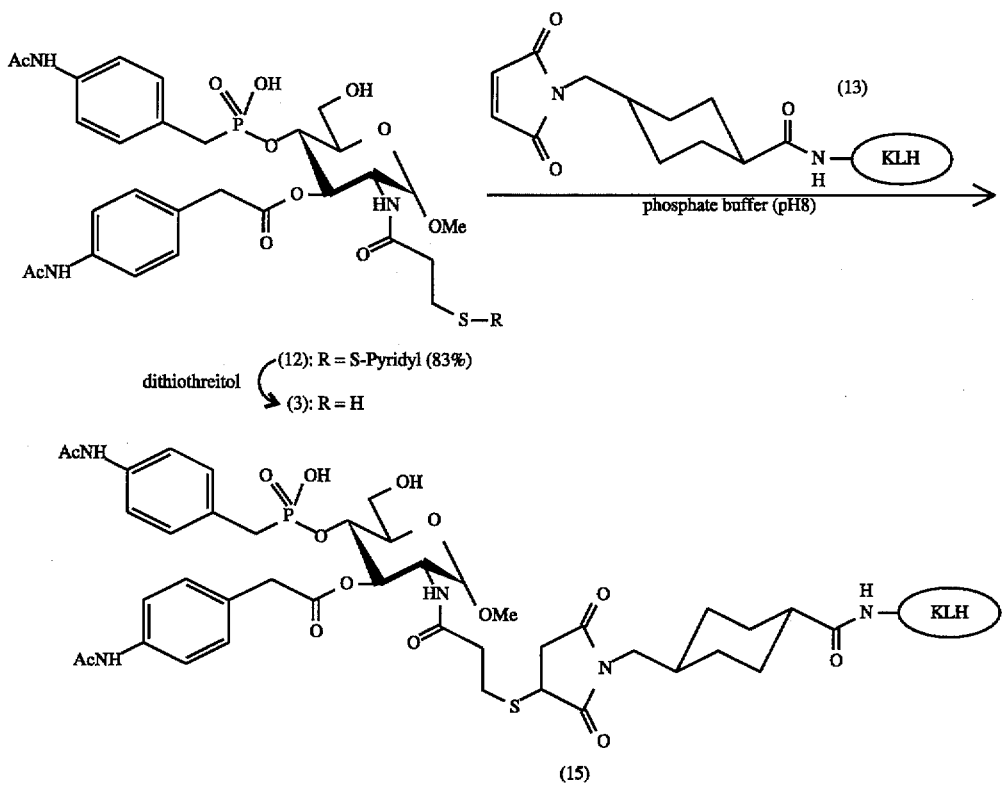

Compound (5), which was prepared through 3 steps from D-glucosamine (4), was reacted with N-acetyl-p-aminophenylacetic acid(6) in the presence of N,N-dimenthylaminopropyl ethylcarbodimide (WSCD) to give ester (7). Alcohol (8) was synthesized by regioselective cleavage of 4 methoxy-benzylidyne acetal in (7) by treatment with sodium borohydride and trifluoroacetic acid. Alcohol (8) was reacted with N-acetyl-p-aminobenzylphosphonic acid (9) in the presence of dicyclohexylcarbodiimide (DCC) in pyridine to afford phosphonate (10). After removing deprotection of both N-benzyl and O-benzyl group of (10) by hydrogenolysis, the resulting phosphonate was conjugated with N-succinimidyl 3-(2-pyridylditrio) propionate (SPDP: 11) to give amide (12). Removal of thiopyridyl group of (12) by treatment with dithiothreitol gave hapten (3), which was conjugated with maleimide activated KLH (13) (KLH: Keyhole limpet hemocyanin) through Michael addition to give antigen (15).

Monoclonal antibodies were produced through immunization of BALB/c mouse with the above mentioned antigen (15). Spleen cells of three BALB/c mice (female, 4 weeks old) immunized (four times) with the antigen (15) were prepared to make hybridoma. After cell fusion according to the standard method, hybridomas which produced antibodies specific to the hapten were screened by enzyme-linked immunosorbent assay (ELISA). Repeat of cloning with limited dilution method gave clones, Crude antibodies were purified by $(NH_4)_2SO_4$ precipitation, cation exchange chromatography, and protein G affinity chromatography.

Finally, the resulting antibodies were screened to be catalytic. The catalytic antibodies described here are able to catalyze regio- and stereoselective hydrolysis of the ester group in the acyl-protected carbohydrates as shown below.

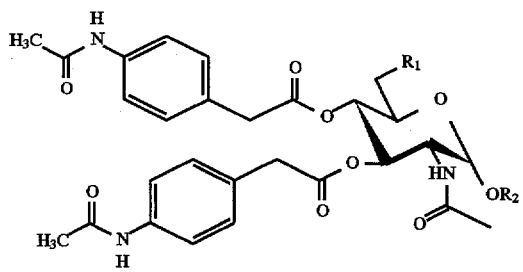

In the above formula, R1 is H, OH, F, OCH3, monosaccharides, oligosaccharides or a group having the formula:

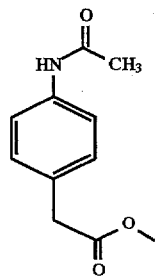

and $R_2$ is H, $CH_3$, monosaccharide and/or oligosaccharide.

For the screening of catalytic activity, 6-fluoro derivative (1) was used as a substrate. This compound is synthesized as shown below: Compound (17) was treated with N,N-dimenthylaminosulfurtrifluoride (DAST) to give compound

(18) which was conjugated with N. N-acetyl-p-aminophenylacetic acid (6) in the presence of N-dimenthylaminopropyl ethylcarbodimide (WSCD) to afford substrate (1).

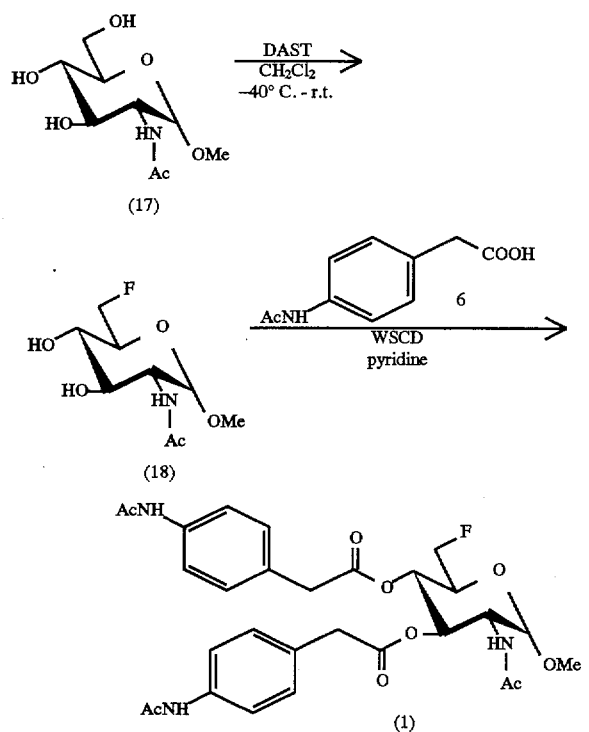

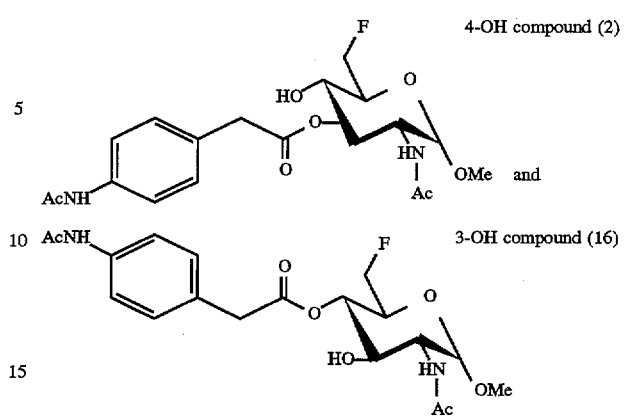

In fact, 3-OH(16) and 4-OH(2) were produced with ratio of 1:4 in the hydrolysis of substrate (1) under the condition of 10% DMSO/Tris HCl (50 mM, pH 8.2) in the absence of the antibody. On the other hand, in the presence of the antibody 17E11 the production ratio of 3-OH and 4-OH was 20.

Furthermore, regio- and stereoselectivity of antibody 17E11 was examined using acylated glucose derivative (21) at C-2, 3 and 4 positions as shown below.

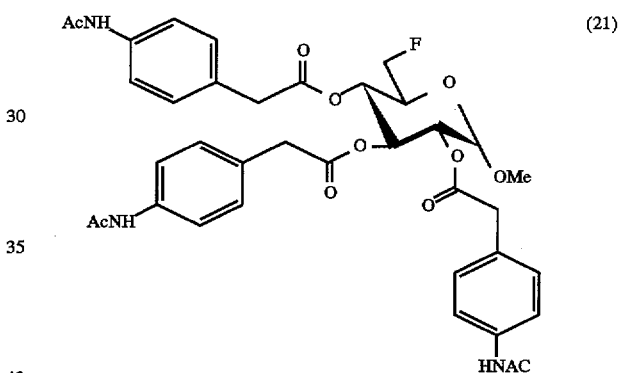

In addition, the other 6-fluoro derivatives of acylated carbohydrates mentioned above were prepared by the same method as substrate (1).

Hydrolytic activities were examined for 12 among 30 antibodies. Hydrolysis of compound (1) with the 12 antibodies were examined in 10% DMSO/Tris HCl (50 mM, pH 8.2), following the production of 4-OH (2) with high performance liquid chromatography (HPLC, 254 nm). The HPLC analysis indicated catalytic activity of six antibodies (17E11, 20C6, 28D6, 33H8, 25A1,2B2). Among 6 catalytic antibodies, antibody 17E11 was the most active. in the reaction with 17E11, substrate (1) disappeared completely in 40 minutes. Hydrolysis with 17E11 followed Michaelis-Menten kinetic and was inhibited by an addition of hapten (3). Rate enhancement (kcat/kuncat) was 2700-fold. Kinetic parameters of hydrolytic reaction with 17E11 is as follows:

TABLE 1

Kinetic parameters of hydrolytic reaction of antibody 17E11

| $K_m$[a] | $K_{cat}$[a] | $k_{cat}/k_{uncat}$[b] |
|---|---|---|
| 4.75 μM | 0.163 min$^{-1}$ | 2.7 × 10$^3$ |

[a]Substrate: compound(1)
[b]$k_{uncat}$ = 6.05 × 10$^{-5min-1}$

Regio- and stereoselectivity of ester hydrolysis with antibody 17E11 was examined.

Hydrolysis of 6-fluoro derivative (1) gave 4-OH (2) and 3-OH (16) as shown below.

Despite the fact that ester at C-2 position was faster to be hydrolyzed in the background reaction, antibody 17E11 hydrolyzed predominantly the ester group at the C-4 position (ratio; 4-OH: 3-OH: 2-OH=20: 1:2) to prove the high regioselectivity of the catalytic antibody.

The antibodies elicited against phosphonate (3) were proved to catalyze regioselective and stereoselective hydrolysis of protected carbohydrates with the same ester protecting group. Herein, it is described that catalytic antibodies witch regioselectivity at C-4 position can be produced by the immunization with hapten bearing phosphonate moiety at the C-4 position. It is clear that antibodies elicited against hapten bearing phosphonate moiety at the C-2 or C-3 position will show catalytic activity of regioselective hydrolysis at the C-2 or C-3 position.

The antibodies elicited against phosphonate (3) were found to regioselectively hydrolyse ester group at the C-4 position of not only compound (1) but also compound (21). This result indicates that the antibodies can recognize only ester groups at C-3 and 4. Therefore, gluco-type hexapyranose C-3 and 4 ester derivatives possessing varieties of substituents at C-1, 2, and 6 positions have potential to be good substrates for these catalytic antibodies. Thus, applicability of these catalytic antibodies to wide range of substrates is strongly expected.

Therefore, the antibodies can be expected to hydrolyze C-4 ester group in manno-type hexapyranoses, because manno-type hexapyranoses are different from gluco-type hexapyranoses in configuration at C-2 position. On the other hand, the antibodies are not applicable to galacto-type hexapyranoses because they are different from gluco-type hexapyranoses in configuration at C-4 position. The method described here allows us to develop catalytic antibodies which regioselectively hydrolyze ester group at desired position in galacto-type, gluco-type and other monosaccharides.

The method is expected to be applicable not only to monosaccharides but also to oligosaccharides. Therefore, even complex branched oligosaccharides involving gluco-type, galacto-type and manno-types hexapyranoses could be easily synthesized by repeated deprotection by the catalytic antibodies and glycosyl reaction. Since this invention simplifies conventional complicated synthetic method for oligosaccharides, it may be expected to develop solid phase synthesis of oligosaccharides using the catalytic antibodies.

The following detailed examples are presented by way of illustration of certain specific embodiments of the invention. The examples are representative only and should not be construed as limiting the present invention in any respect.

BRIEF DESCRIPTION OF THE DRAWINGS

In the accompanying drawing.

EXAMPLE

Example 1

Synthesis of Hapten (3)

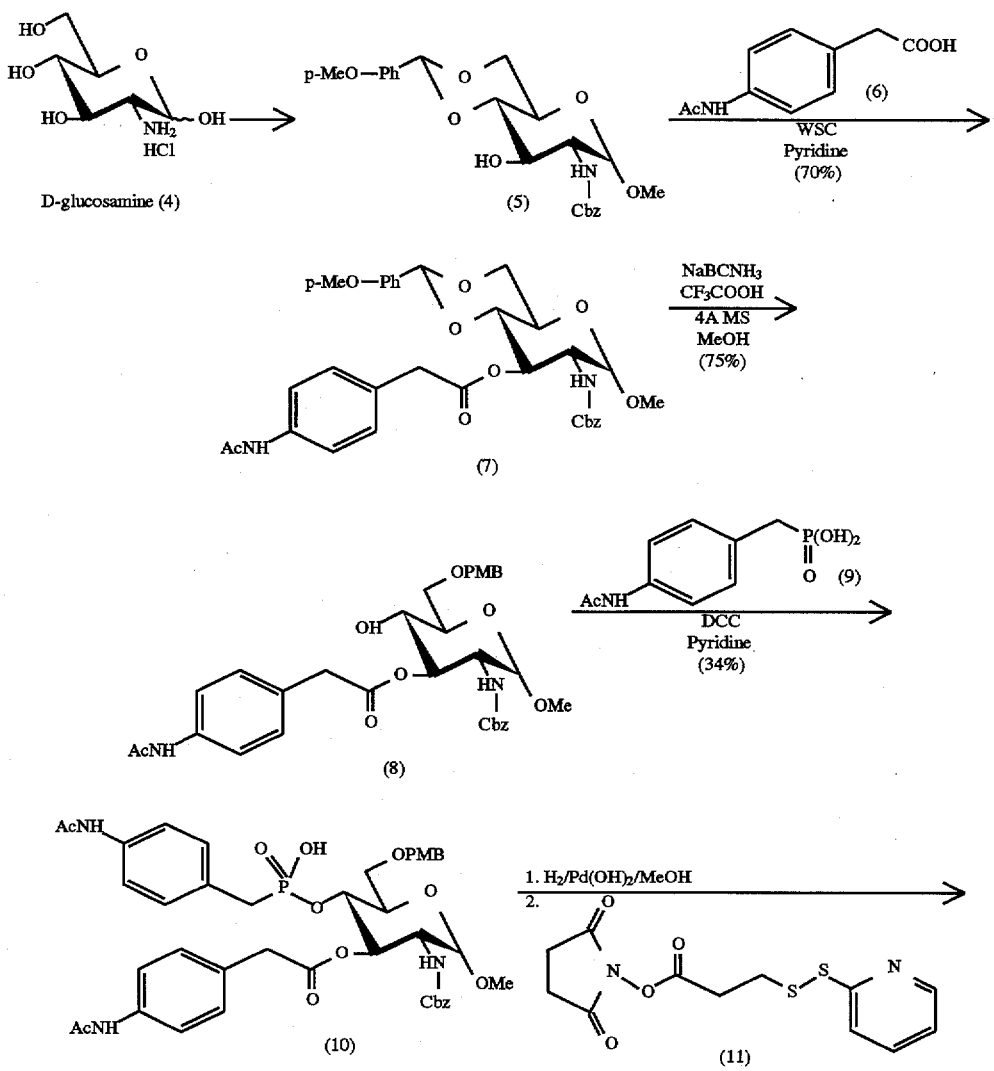

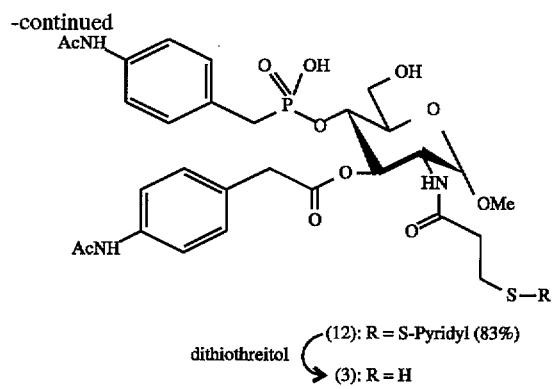

1. Synthesis of compound (7)

Figure 1:
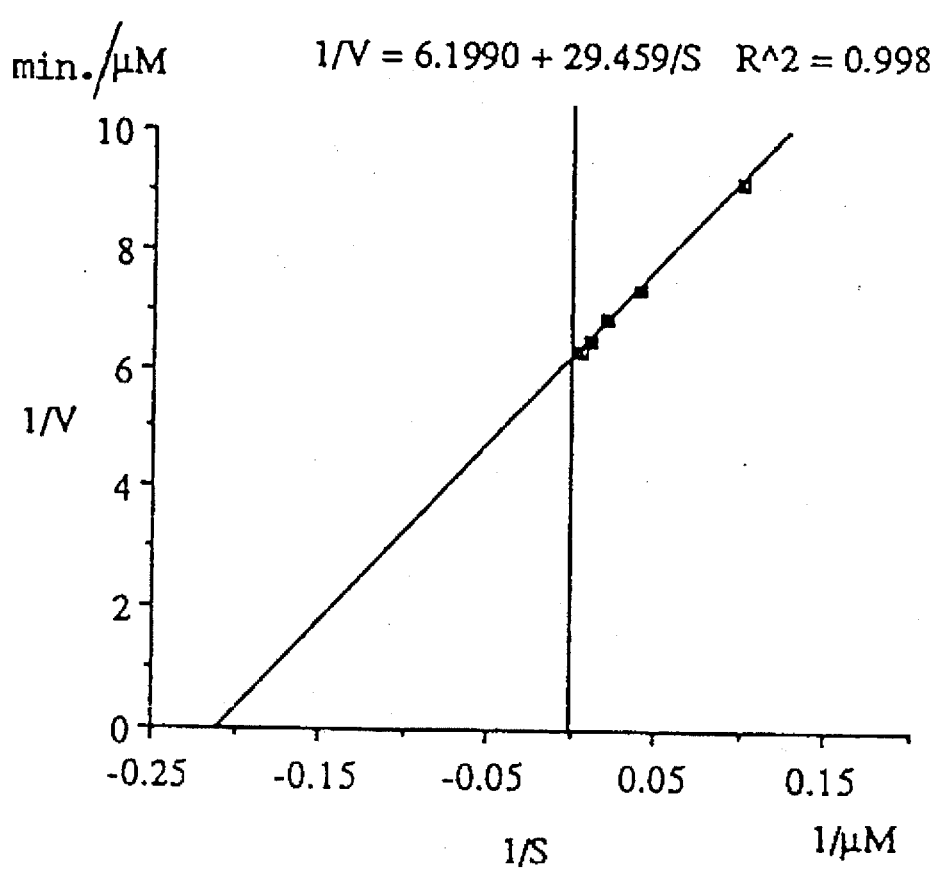
FIG. 1 shows catalytic activity of the antibody 17E11 on Compound (1). The graph was prepared using Line-Weaver-Burk double reciprocal plot method.

Compound (5) was prepared as described in literature (R. Johansson and B. Samuelsson, J. Chem. Soc., Perkin Trans 1, 2371 (1984)). A mixture of compound (5) (2.80 g, 6.28 mmol), N-acetyl-4-aminophenylacetic acid (1.33 g, 6.91 mmol), 1-(3-dimethylaminopropyl)-3-ethylcarbodiimide hydrochloride (1.32 g, 6.91 mmol) and pyridine (20 mL) was stirred overnight at ambient temperature. After concentration in vaccuo, the residue was taken up into AcOEt and washed successively with 1N hydrochloric acid, saturated aqueous $NaHCO_3$ and brine. The organic layer was dried ($MgSO_4$), concentrated and chromatographed (silica gel, AcOEt-n hexane 1:2) to give compound (7) (2.74 g, 70%). IR (KBr) $\nu_{max}$ 1736, 1670, 1654, 1614 cm$^{-1}$; $^1$H—NMR (500 MHz, 10% $CD_3OD$ in $CDCl_3$) δ 2.10 (s, 3H, $CH_3$), 3.38 (s, 3H, $OCH_3$), 3.48 (d, J=15.8 Hz, 1H, CHPh), 3.53 (d, J=15.8 Hz, 1H, CHPh), 3.67 (dd, J=9.7, 10.1 Hz, 1H, H-4), 3.75 (dd, J=10.4, 10.4 Hz, 1H, H-6), 3.80 (s, 3H, $OCH_3$), 3.83 (dd, J=3.2, 10.4 Hz, H-6), 4.05 (ddd, J-9.5, 9.5, 3.2 Hz, 1H, H-5), 4.25 (dd, J=3.8, 9.7 Hz, 1H, H-2), 4.72 (d, J=3.2 Hz, 1H, H-1 ), 5.02 (brs, 2H, $OCH_2Ph$), 5.30 (dd, J=9.7, 9.7 Hz, 1H, H-3), 5.42 (s, 1H, benzylic), 6.80 (d, J=10.6 Hz, 2H, aromatic), 7.20–7.46 (m, 11H, aromatic); FAB MS m/e 621 [M+H]$^+$.

2. Synthesis of compound (8)

A solution, at 0° C., of trifluoroacetic acid (1.5 mL) in DMF (5 mL) was added dropwise to a stirred mixture containing compound (7) (420 mg, 0.68 mmol), sodium cyanoborohydride (590 mg, 9.39 mmol), and 3Å molecular sieves (1.0 g) in DMF (8 mL). After 7 hr the mixture was filtered through Celite and poured into ice-cooled saturated aqueous $NaHCO_3$. The aqueous phase was extracted with $CH_2Cl_2$ and the combined extracts were washed with saturated aqueous $NaHCO_3$, dried ($MgSO_4$), and concentrated. The residue was purified by column chromatography (silics gel, AcOEt-n-hexane 2:1) to give compound (8) (320 mg, 75%). IR (KBr) $\nu_{max}$ 3438, 1732, 1670, 1650, 1610 cm$^{-1}$; $^1$H-NMR (500 MHz, 10% $CD_3OD$ in $CDCl_3$) δ 2.07 (s, 3H, $CH_3$), 2.82 (d, J=15.8 Hz, 1H, CHPh), 2.99 (d, J=15.8 Hz, 1H, CHPh), 3.35 (s, 3H, $OCH_3$), 3.46 (d, J=15.2 Hz, 1H, H-6), 3.51 (d, J=15.2 Hz, 1H, H-6), 3.68–3.70 (m, 2H, H-2, H-4), 3.80 (s, 3H, $OCH_3$), 3.96 (ddd, J=9.5, 8.7, 3.2 Hz, 1H, H-5), 4.48 (d, J=10.7 Hz, 1H, OCHAr), 4.50 (d, J=1 0.7 Hz, 1H, OCHAr), 4.70 (d, J=3.2 Hz, 1H, H-1), 5.02 (s, 2H, $OCH_2Ph$), 5.09 (dd, J=9.4, 9.4 Hz, 1H, H-3), 6.88 (d, J=7.2 Hz, 2H), 7.07 (d, J=6.8 Hz, 2H), 7.22 (d, J=7.2 Hz, 2H), 7.26–7.58 (m, 7H); FAB MS m/e 623 [M+H]$^+$.

3. Synthesis of compound (10)

A mixture of compound (8) (520 mg, 0.835 mmol), N-acetyl-4-aminobenzylphosphonic acid (9) (1.30 mg, 8.72 mmol), dicyclohexylcarbodiimide (1.80 g, 8.72 mmol), and pyridine (40 mL) was stirred overnight at 40° C. After concentration in vaccuo, the residue was purified by high performance liquid chromatography (ODS, 10×250 mm, 3 mL/min, 254 nm, 45% acetonitrile-0.1% aqueous trifluoroacetic acid, 11 min.) and lyophiiized to give compound (10) (248 mg, 34%). $^1$H-NMR (600 MHz, 5% $CD_3OD$ in $CDCl_3$) δ 2.08 (s, 3H, $CH_3$), 2.12 (s, 3H, $CH_3$), 2.82 (d, J=21.6 Hz, 2H, $PCH_2Ar$), 3.37 (s, 3H, $OCH_3$), 3.76 (s, 3H, $OCH_3$), 3.85 (ddd, J=10.8, 10.8, 3.4 Hz, 1H, H-5), 4.04 (m, 1H, H-4), 4.36 (d, J=1 1.3 Hz, 1H, OCHAr), 4.49 (d, J=11.3 Hz, 1H, OCHAr), 4.67 (d, J=3.4 Hz, 1H, H-1), 5.08 (s, 2H, $CH_2Ph$), 5.23 (dd, J=9.2, 9.2 Hz, 1H, H-3), 6.84 (d, J=8.6 Hz, 2H, aromatic), 6.94 (d, J=7.6 Hz, 2H, aromatic), 7.10 (d, J=7.6 Hz, 2H, aromatic), 7.19 (d, J=8.6 Hz, 2H, aromatic), 7.22–7.29 (m, 5H, aromatic), 7.33 (d, J=7.6 Hz, 2H, aromatic), 7.37 (d, J=7.6 Hz, 2H, aromatic); FAB MS m/e 832 [M–H]$^-$.

4. Synthesis of compound (12)

A mixture of compound (10) (25 mg, 30 μmol), 20% Pd(OH)$_2$ on carbon (50 mg), and MeOH (10 mL) was stirred under H$_2$ atmosphere for 0.5 hr and filtered through Celite. The flitrate was concentrated and taken up into phosphate buffer (50 mM, pH 8.0, 1 mL). To the solution was added N-succinimidyl 3-(2-dithiopyridyl)propionate (11) (15 mg, 48 μmol) and stirred for 3 hr. The mixture was purified by high performance liquid chromatography (ODS, 10×250 mm, 3 mL/min, 254 nm, acetonitrile (graduent 20 to 60%; 20 min)-0.1% aqueous trifluoroacetic acid: 11.5 min.) and lyophilized to give compound (12) (20 mg, 83%). $^1$H-NMR (500 MHz, $CD_3OD$ in $CDCl_3$) δ 2.03 (s, 3H, $CH_3$), 2.06 (s, 3H, $CH_3$), 2.33 (dt, J=15.2, 7.6 Hz, 1H, $SCH_2CH$), 2.42 (dt, J=15.2, 7.6 Hz, 1H, $SCH_2CH$), 2.89 (t, 7.6 Hz, 2H, $SCH_2CH_2$), 2.92 (d, J=21.7 Hz, 2H, $PCH_2Ar$), 3.30 (s, 3H, $OCH_3$), 3.50 (dd, J=13.1, 5.1 Hz, 1H), 3.61 (dd, J=13.1, 2.4 Hz, 1H), 3.68 (dd, J=5.1, 2.4 Hz, 1H), 4.29 (m, 1H, H-4), 4.61 (d, J=4.0 Hz, 1H, H-1), 5.16 (dd, J=7.6, 7.6 Hz, 1H, H-3), 7.18 (d, J=6.4 Hz, 2H, aromatic), 7.20 (d, J-6.4 Hz, 2H, aromatic), 7.25 (dd, J=8.6, 7.8 Hz, 1H, Py-H$_5$), 7.48 (d, J=6.4 Hz, 2H, aromatic), 7.51 (d, J=6.4 Hz, 2H, aromatic), 7.72 (d, J=8.6 Hz, 1H, Py-H$_3$), 7.82 (dd, J=8.6, 8.6 Hz, 1H, Py-H$_4$), 8.44 (d, J=7.8 Hz, 1H, Py-H$_6$); FAB MS m/e 445 (M+); FAB MS m/e 775 [M–H]$^-$.

5. Synthesis of compound (3)

A solution of compound (12) (15 mg, 19 μmol) and dithiothreitol (2.5 g, 62.5 mmol) in phosphate buffer (50 mM, pH 8.0, 1 mL) was stirred under Argon atmosphere for 2 hr. The mixture was purified by high performance liquid chromatography (ODS, 10×250 mm, 3 mL/min, 254 nm, acetonitrile(graduent 20 to 60 %; 20 min)-0.1% aqueous trifluoroacetic acid: 9.4 min.) and lyophilized to give compound (3) (9 mg, 71%). $^1$H-NMR (500 MHz, 5% CD$_3$OD in CDCl$_3$) δ 2.09 (s, 3H, CH$_3$), 2.11 (s, 3H, CH$_3$), 2.26 (dt, J=15.2, 7.6 Hz, 1H, SCH$_2$CH), 2.36 (dt, J=15.2, 7.6 Hz, 1H, SCH$_2$CH)), 2.70 (t, J=7.6 Hz, 2H, SCH$_2$CH$_2$), 3.04 (d, J=22.2 Hz, 2H, PCH$_2$Ar), 3.38 (s, 3H, OCH$_3$), 3.53 (dd, J=13.1, 5.1 Hz, 1H, H-6), 3.61 (dd, J=13.1, 2.4 Hz, 1H, H-6), 3.68 (ddd, J=2.4, 5.1, 9.1 Hz, 1H), 4.23 (dd, J=4.0, 9.1 Hz, 1H, H-2), 4.40 (ddd, J=6.3, 9.1, 9.1 Hz, 1H, H-4), 4.63 (d, J=4.0 Hz, 1H, H-1), 5.34 (dd, J=9.1, 9.1 Hz, 1H, H-3), 7.18 (d, J=6.4 Hz, 2H, aromatic), 7.20 (d, J=6.4 Hz, 2H, aromatic), 7.48 (d, J=6.4 Hz, 2H, aromatic), 7.51 (d, J=6.4 Hz, 2H, aromatic); FAB MS m/e 666 [M–H]$^-$.

Example 2

Conjugation of Hapten and Carrier Proteins

Example 3

Synthesis of Substrate Compound (1)

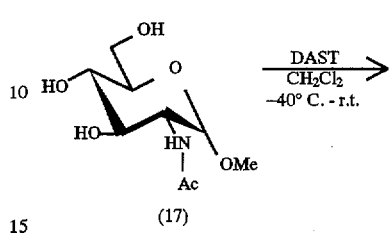

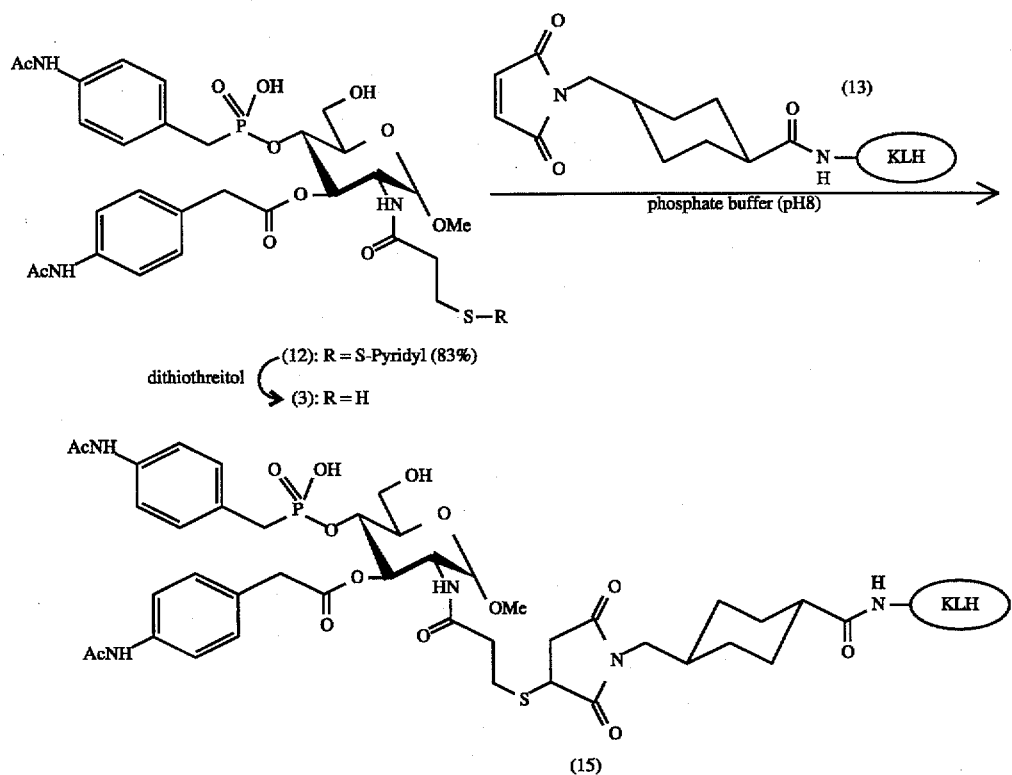

To a solution of maleimide-activated KLH (13) (4.46 mg) in conjugation buffer (83 mM sodium phosphate, 0.1M EDTA, 0.9M NaCl, pH7.2 800 µL) was added a solution of compound (3) (4.0 mg, 6.0 µmol) in conjugation buffer (83 mM sodium phosphate, 0.1M EDTA, 0.9M NaCl, pH7.2, 200 µL) at ambient temperature and allowed to stand for 3 hrs. The mixture was chromatographed (Sephadex-25, purification buffer; 83 mM sodium phosphate, 0.9M NaCl, pH7.2 ) to give immunogen (15) (protein concentration 2.86 mg/mL; Bradford's method). The degree of conjugation was estimated to be 11 haptens/KLH by titrating unreactied sulfhydryl group using Ellman's reagent.

Hapten-BSA conjugate was prepared in a similar manner and used for ELISA to measure titer of antibody elicited by immunization.

-continued

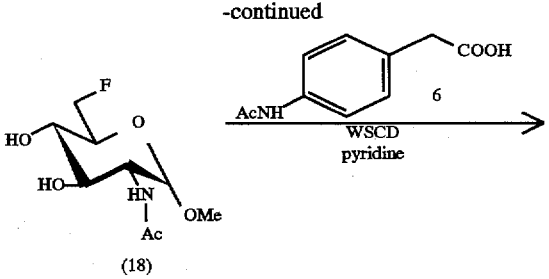

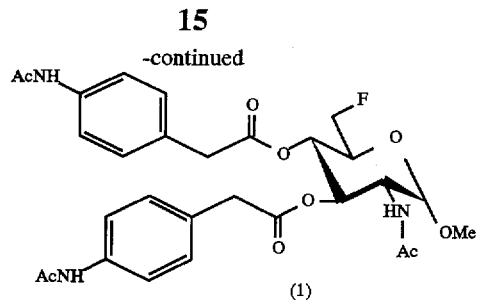

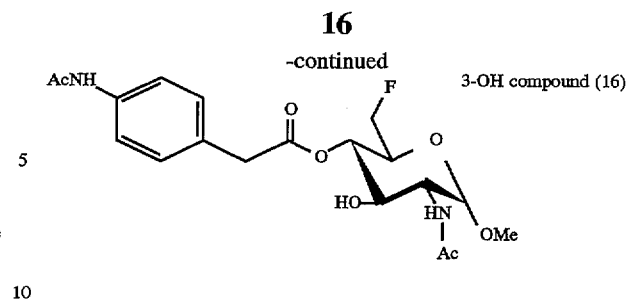

1. Synthesis of compound (18)

To a suspension of methyl 2-acetamido-α-D-glucopyranoside (17) (250 mg, 1.06 mmol) in $CH_2Cl_2$ at −40° C. was added diethylaminosulfur trifluoride (0.59 mL, 4.46 mmol). The cooling bath was removed, and the mixture was allowed to stir for 1 hr as it warmed to ambient temperature. The mixture was cooled to −10° C., quenched via addition of MeOH (10 mL) and $NaHCO_3$ (1 g). After concentration, the residue was taken up into AcOEt and washed with brine. The organic phase was dried ($MgSO_4$), concentrated, and chromatographed (silica gel, AcOEt only) to give compound (18) (163 mg; 65%). $^1$H-NMR (500 MHz, $CDCl_3$) δ 1.75 (s, 3H, $CH_3$), 3.38 (s, 3H, $OCH_3$), 3.48 (dd, J=9.7, 9.7 Hz, 1H, H-4), 3.61 (dd, J=9.7, 9.7 Hz, 1H, H-3), 3.72 (m, 1H, H-2), 3.74 (m, 1H, H-5), 4.62 (dd, J=−46.8, 3.6 Hz, 2H, H-6), 4.72 (d, J=3.6 Hz, 1H, H-1); FAB MS m/e 226 $[M+H]^+$.

2. Synthesis of compound (1)

A mixture of compound (18) (72 mg, 0.30 mmol), N-acetyl-4-aminophenylacetic acid (174 mg, 0.90 mmol), 1-(3-dimethylaminopropyl)-3-ethylcarbodiimide hydrochloride (230 mg, 1.20 mmol) and pyridine (4 mL) was stirred overnight at ambient temperature. After concentration in vaccuo, the residue was taken up into AcOEt and washed successively with 1N hydrochloric acid, saturated aqueous $NaHCO_3$ and brine. The organic phase was dried ($MgSO_4$), concentrated and chromatographed (silica gel, AcOEt-n-hexane 4:1 to AcOEt only) to give compound (1) (141 mg, 80%). $^1$H-NMR (500 MHz, 10% $CD_3OD$ in $CDCl_3$) δ 1.75 (s, 3H, $CH_3$), 2.12 (s, 3H, $CH_3$), 2.13 (s, 3H, $CH_3$), 3.26 (d, J=14.4 Hz, 1H, CHAr), 3.34 (d, J=14.4 Hz, 1H, CHAr), 3.37 (d, J=14.4 Hz, 1H, CHAr), 3.38 (d, J=14.4 Hz, 1H, CHAr), 3.39 (s, 3H, $OCH_3$), 3.90 (m, 1H, H-5), 4.18 (dd, J=3.2, 10.8 Hz, H-2), 4.32 (ddd, J=4.3, 10.8, 46.8 Hz, H-6), 4.38 (ddd, J=2.4, 10.8, 46.8 Hz, H-6), 4.69 (d, J=3.2 Hz, 1H, H-1), 5.08 (dd, J=10.8, 10.8 Hz, 1H, H-4), 5.22 (dd, J=10.8, 10.8 Hz, 1H, H-3), 7.08 (d, J=10.6 Hz, 2H, aromatic), 7.10 (d, J=10.6 Hz, 2H, aromatic), 7.43 (d, J=10.6 Hz, 2H, aromatic), 7.48 (d, J=10.6 Hz, 2H, aromatic); FAB MS m/e 588 $[M+H]^+$.

Preparation 1

Synthesis of compounds (2) and (16)

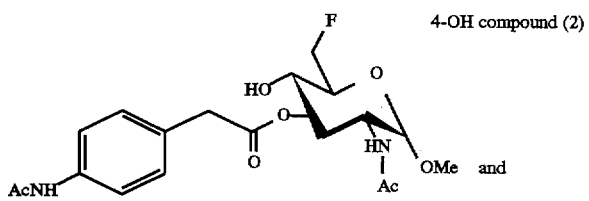

A mixture of compound (18) (41 mg, 0.30 mmol), N-acetyl-4-aminophenylacetic acid (39 mg, 0.20 mmol), 1-(3-dimethylaminopropyl)-3-ethylcarbodiimide hydrochloride (42 mg, 0.22 mmol) and pyridine (4 mL) was stirred overnight at ambient temperature. After concentration in vaccuo, the residue was taken up into AcOEt and washed successively with 1N hydrochloric acid, saturated aqueous $NaHCO_3$ and brine. The organic phase was dried ($MgSO_4$) and concentrated. The residue was purified by preparative TLC (silica gel, AcOEt-n-hexane 4:1) to give compound (2) (Rf=0.4) and compound (16) (Rf=0.35, mg).

Compound (2): $^1$H-NMR (500 MHz, 5% $CD_3OD$ in $CDCl_3$) δ 1.71 (s, 3H, $CH_3$), 2.12 (s, 3H, $CH_3$), 3.40 (s, 3H, $OCH_3$), 3.58 (d, J=14.4 Hz, 1H, CHAr), 3.61 (d, J=14.4 Hz, 1H, CHAr), 3.67 (dd, J=10.1, 10.1 Hz, 1H, H-4), 3.73 (m, 1H, H-5), 4.19 (dd, J=10.1, 3.4 Hz, 1H, H-2), 4.63 (dd, J=3.4, 10.8, 46.7 Hz, 1H, H-6), 4.67 (d, J=3.6 Hz, 1H, H-1 ), 4.68 (dd, J=4.3, 10.8, 46.7 Hz, 1H, H-6), 5.10 (dd, J=10.1, 9.5 Hz, 1H, H-3),, 7.18 (d, J=10.6 Hz, 2H, aromatic), 7.48 (d, J=10.6 Hz, 2H, aromatic); FAB MS m/e 413 $[M+H]^+$.

Compound (16): $^1$H-NMR (500 MHz, 5% $CD_3OD$ in $CDCl_3$) δ 1.75 (s, 3H, $CH_3$), 2.13 (s, 3H, $CH_3$), 3.38 (s, 3H, $OCH_3$), 3.61 (d, J=14.4 Hz, 1H, CHAr), 3.63 (d, J=14.4 Hz, 1H, CHAr), 3.68 (dd, J=10.1, 8.0 Hz, 1H, H-3), 3.75 (m, 1H, H-5), 4.19 (m, 1H, H-2), 4.63 (dd, J=46.7, 11.1,3.4 Hz, 1H, H-6), 4.68 (dd, J=46.7, 11.1,4.3 Hz, 1H, H-6), 4.70 (d, J=3.4 Hz, 1H, H-1 ), 4.89 (dd, J=10.1, 10.1 Hz, 1H, H-4), 7.22 (d, J=10.6 Hz, 2H, aromatic), 7:49 (d, J=10.6 Hz, 2H, aromatic); FAB MS m/e 41 3 $[M+H]^+$.

Example 4

Synthesis of Substrate Compound (21)

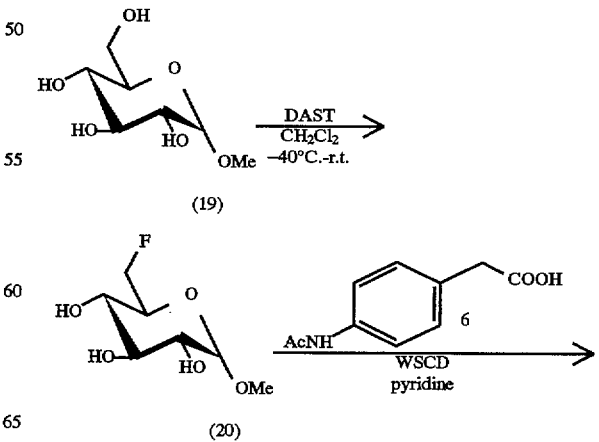

-continued

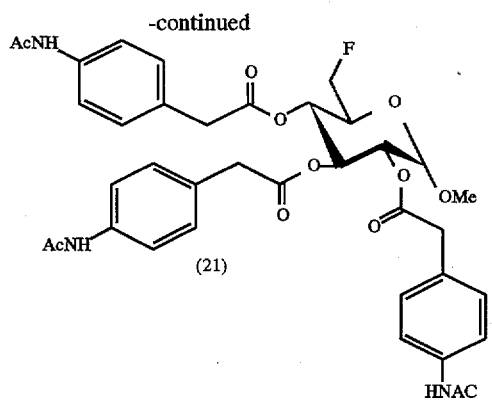

(21)

1. Synthesis of compound (20)

To a suspension of methyl α-D-glucopyranoside (19) (970 mg, 5.0 mmol) in CH$_2$Cl$_2$ at −50° C. was added diethylaminosulfur trifluoride (3.75 mL, 28.4 mmol). The cooling bath was removed, and the mixture was allowed to stir for 5 hr as it warmed to ambient temperature. The mixture was cooled to −10° C., quenched via addition of MeOH (20 mL) and NaHCO$_3$ (3 g). After concentration, the residue was taken up into AcOEt and washed with brine. The organic phase was dried (MgSO$_4$), concentrated, and chromatographed (silica gel, 10% MeOH in AcOEt) to give compound (20) (618 mg, 63%), $^1$H-NMR (500 MHz, CDCl$_3$) δ 1.75 (s, 3H, CH$_3$), 3.38 (s, 3H, OCH$_3$), 3.48 (dd, J=9.7, 9.7 Hz, 1H, H-4), 3.61 (dd, J=9.7, 9.7 Hz, 1H, H-3), 3.72 (m, 1H, H-2), 3.74 (m, 1H, H-5), 4.62 (dd, J=46.8, 3.6 Hz, 2H, H-6), 4.72 (d, J=3.6 Hz, 1H, H-1); FAB MS m/e 226 [M+H]$^+$.

2. Synthesis of compound (21)

A mixture of compound (21) (50 mg, 0.255 mmol), N-acetyl-4-aminophenylacetic acid (350 mg, 1.78 mmol), 1-(3-dimethylaminopropyl)-3-ethylcarbodiimide hydrochloride (490 mg, 2.55 mmol) and pyridine (5 mL) was stirred overnight at ambient temperature. After concentration in vaccuo, the residue was taken up into AcOEt and washed successively with 1N hydrochloric acid, saturated aqueous NaHCO$_3$ and brine. The organic phase was dried (MgSO$_4$), concentrated and chromatographed (silica gel, AcOEt-n-hexane 4:1 to AcOEt only) to give compound (21) (147 mg, 80%). $^1$H-NMR (600 MHz, 5% CD$_3$OD in CDCl$_3$) δ 2.10 (s, 3H, CH$_3$), 2.15 (s, 3H, CH$_3$), 2.16 (s, 3H, CH$_3$), 3.05 (d, J=15.1 Hz, 1H, CHAr), 3.11 (d, J=15.1 Hz, 1H, CHAr), 3.28–3.33 (m, 2H, CH$_2$Ar), 3.39 (s, 3H, OCH$_3$), 3.40–3.48 (m, 2H, CH$_2$Ar), 3.94 (dd, J=16.8, 7.4 Hz, 1H, H-5), 4.33 (ddd, J=3.6, 9.5, 42.8 Hz, H-6), 4.40 (dd, J=9.5, 42.8 Hz, 1H, H-6), 4.85 (dd, J=8.1,2.8 Hz, 1H, H-2), 4.92 (d, J=2.8 Hz, 1H, H-1), 5.03 (dd, J=8.1,8.1 Hz, lH, H-4), 5.48 (dd, J=8.1, 8.1 Hz, 1H, H-3), 6.93 (d, J=8.4 Hz, 2H, aromatic), 7.07 (d, J=8.4 Hz, 2H, aromatic), 7.12 (d, J=8.4 Hz, 2H, aromatic), 7.38 (d, J=8.4 Hz, 2H, aromatic), 7.44 (d, J=8.4 Hz, 2H, aromatic), 7.45 (d, J=8.4 Hz, 2H, aromatic); FAB MS m/e 722 [M+H]$^+$.

Example 5

Immunization

Four-week-old BALB/c mice were immunized with the KLH conjugates of compound (3) (i.p., 50 mg per mouse in complete Freund's adjuvant), and a booster injection was administered once every 10 days. 7 days after the secondary booster injection, antibody titer was 1:10$^6$ (measured by an ELISA using BSA conjugates of compound (3), biotinilated anti mouse IgG, avidin and biotinilated peroxidase). One month after the secondary booster injection, the final booster injection was administered (i.v., 100 mg in PBS).

Example 6

Hybridoma Production

Three days after the final booster injection, 5.4–10$^8$ spleen cells were fused with 9.6–10$^7$X63/Ag8653 myeloma cells. Cells were distributed into 30×96 well dishes containing 10$^5$ per well of feeder cells (mouse thymus) and HAT selection medium (0.1 mM hypoxanthine, 0.4 mM aminopterin, 0.016 mM thymidine, 10% fetal calf serum and RPMI medium) with 10% CO$_2$ at 37° C. 8 to 14 days after the cell fusion, tissue culture supernatants in wells containing macroscopic colonies were assayed with the BSA conjugates by an ELISA (109 positive wells ). 50 wells were cloned and then 12 single clones were obtained. All of 12 clones produced IgG (by ELISA using anti mouse IgG heavy chain).

Example 7

Purification of Monoclonal Antibodies 12 hybridomas were propagated in complete medium (10% fetal calf serum, RPMI medium), for 7 days. Cell suspension was injected to 8-week-old female BALB/c mice treated by pristane (i.p., 1–10$^7$ cells in PBS ). Two weeks after the injection, 3 to 5 ml of ascitic fluid were drawn. The antibodies from ascitic fluid were precipitated by saturated ammonium sulfate. The concentrated antibodies were next purified by cation-exchange chromatography (S-Sepharose) and affinity chromatography on a protein G, and then 10 to 20 mg of purified antibodies were obtained.

180 µl pre-reaction mixture containing 22 mM purified antibody in 50 mM Tris-HCl, pH8.2, was incubated at room temperature for few minutes. The pre-reaction mixture was added to 20 µl of 1.5 mM compound (1) in DMSO and then mixed well. Hydrolysis rates were measured by monitoring the production of 4-OH via high-performance liquid chromatography (HPLC) on an ODS column eluted with water-acetonitrile (75:25), 0.1% TFA at a flow rate of 1 ml / min, with UV detection at 2.54 nm (retention time, 5.4 min). The reaction rate of each antibody was calculated by this assay, and 6 antibodies were chosen as catalytic antibodies (Table 2). The hybridoma producing antibody 17E11 was deposited with National Institute of Bioscience and Human-Technology Agency of Industrial Science and Technology of Agency of Industrial and Technology (Deposit date: Aug. 27, 1993. Deposit number: FERM P-13824).

TABLE 2

| Antibodies | Reaction rate |
|---|---|
| 17E11 | 3.00 µM/m |
| 20C6 | 2.10 µM/m |
| 28D6 | 0.14 µM/m |
| 33H8 | 0.11 µM/m |
| 25A11 | 0.11 µM/m |
| 2B2 | 0.06 µM/m |

Experiment 1

Measuring of Catalytic Activity to Compound (1)

1. Kinetic Parameters

180 µl pre-reaction mixture containing 1.11 µM purified antibody in 50 mM Tris-HCl, pH8.2, was incubated at room temperature for few minutes. The pre-reaction mixture was added to 20 ml of 2 mM, 1 mM, 500 µM, 250 µM, and 100 µM compound (1) in DMSO and then mixed well. Hydrolysis rates were measured by monitoring the production of 4-OH via high-performance liquid chromatography (HPLC) on an ODS column eluted with water-acetonitrile (75:25), 0.1% TFA at a flow rate of 1 ml /min, with UV detection at 254 nm (retention time, 5.4 min). The kinetic constants were obtained from Lineweaver-Burk plots.

2. Regioselectivity

To a 180 pl of 50 mM Tris-HCl, pH8.2, was added 20 pl of 1.5 µM compound (1) in DMSO and then mixed well. Hydrolysis rates were measured by monitoring the production of 4-OH and 3-OH via high-performance liquid chromatography (HPLC) on an ODS column eluted with water-acetonitrile (75:25), 0.1% TFA at a flow rate of 1 ml /min, with UV detection at 254 nm (retention time, 5.4 min). After 60 minutes the reaction consumed 0.67% of compound (1) and gave 3-OH(0.2 µM) and 4-OH (0.8 µM) in 1:4 ratio.

180 µl pre-reaction mixture containing 1.11 µM purified antibody in 50 mM Tris-HCl, pH8.2, was incubated at room temperature for few minutes. The pre-reaction mixture was added to 20 ml of 1.5 mM compound (1) in DMSO and then mixed well. Hydrolysis rates were measured by monitoring the production of 4-OH and 3-OH via high-performance liquid chromatography (HPLC) on an ODS column eluted with water-acetonitrile (75:25), 0.1% TFA at a flow rate of 1 ml /min, with UV detection at 254 nm (retention time, 5.4 min). After 60 minutes the reaction consumed 26% of compound (1) and gave 3-OH(1.9 µM) and 4-OH (37.1 µM) in 1:20 ratio.

Experiment 2

Measuring of Catalytic Ativity to Compound (21)

To a 30 µl of 250 µM compound (21) in DMSO was added 120 µl of 50 mM Tris-HCl, pH8.2, and then mixed well. Hydrolysis rates were measured by monitoring the production of 2-OH, 3-OH and 4-OH via high-performance liquid chromatography (HPLC) on an ODS column eluted with water-acetonitrile (75:25), 0.1% TFA at a flow rate of 1 ml /min, with UV detection at 254 nm (retention time, 5.4 min). After 100 minutes the reaction consumed 1.7% of compound (21) and gave 2-OH(0.66 µM), 3 -OH(0.07 µM) and 4-OH (0.11 µM)in 1:0.07:0.2 ratio.

120 µl pre-reaction mixture containing 1.25 µM purified antibody in 50 mM Tris-HCl, pH8.2, was incubated at room temperature for few minutes. The pre-reaction mixture was added to 30 µl of 250 µM compound (21) in DMSO and then mixed well. Hydrolysis rates were measured by monitoring the production of 2-OH, 3-OH and4-OH via high-performance liquid chromatography (HPLC) on an ODS column eluted with water-acetonitrile (75:25), 0.1% TFA at a flow rate of 1 ml /min, with UV detection at 254 nm (retention time, 5.4 min). After 94 minutes the reaction 65 consumed 18% of compound (21) and gave 2-OH(0.72 µM), 3-OH(0.43 µM) and 4-OH (7.7 µM) in 1:0.8:12.9 ratio.

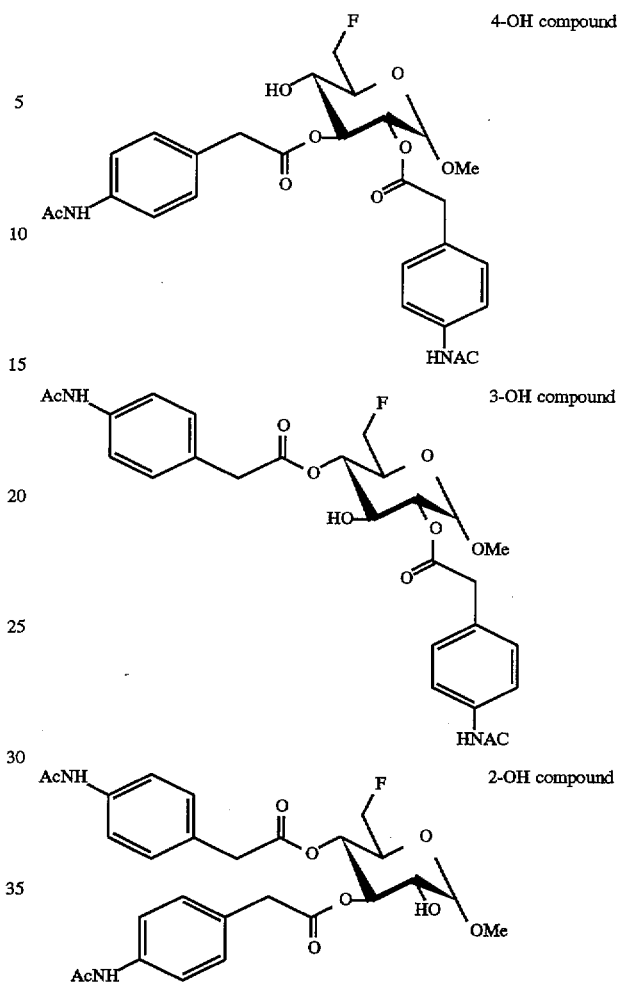

What is claimed is:

1. A method for hydrolytically deprotecting an acylated hydroxy group in a carbohydrate in a regioselective and stereoselective manner, which comprises the step of:

admixing a catalytically effective amount of a catalytic antibody with the carbohydrate containing the acylated hydroxy group, wherein the catalytic antibody specifically hydrolyzes the acylated hydroxy group in the carbohydrate in a regioselective and stereoselective manner, thereby deprotecting the acylated hydroxy group in the carbohydrate in a regioselective and stereoselective manner, said catalytic antibody being produced by immunizing an animal using a compound, as a hapten, which is thought to be a transition state analog of desired hydrolysis of the carbohydrate containing the acylated hydroxy group.

2. The method of claim 1, wherein the carbohydrate comprises one or more monosaccharides, and wherein the acylated hydroxy group to be deprotected is located at the C-4 position in a monosaccharide.

3. The method of claim 1, which comprises the steps of:

(a) preparing a protected carbohydrate by acylation of all hydroxy groups in the carbohydrate with a carboxyl compound, and (b) admixing a catalytically effective amount of a catalytic antibody with the carbohydrate, wherein the catalytic antibody specifically hydrolyzes a single acylated hydroxy group in the carbohydrate in a regioselective and stereoselective manner, thereby deacylating the single acylated hydroxyl group in the carbohydrate in a regioseleCtive and stereoselective manner.

4. The method of claim 1, wherein the carbohydrate comprises one or more monosaccharides, and wherein the acylated hydroxy group to be deprotected is located at the C-4 position in a monosaccharide.

5. The method of claim 1, which comprises the steps of:
(a) preparing a protected carbohydrate comprising an oligosaccharide by acylation of all hydroxy groups in the oligosaccharide with a carboxyl compound, and
(b) admixing a catalytically effective amount of a catalytic antibody with the oligosaccharide, wherein the catalytic antibody specifically hydrolyzes a single acylated hydroxy group at a non-reducing end of the oligosaccharide in a regioselective and stereoselective manner, thereby deacylating the single acylated hydroxy group at the non-reducing end of the oligosaccharide in a regioselective and stereoselective manner.

6. The method of claim 1, wherein the carbohydrate comprises an oligosaccharide having a non-reducing end monosaccharide, and wherein the acylated hydroxy group to be deprotected is located at the C-4 position in the non-reducing end monosaccharide of the oligosaccharide.

7. The method of claim 1, wherein the catalytic antibody is produced by immunization of an animal with the following compound as a hapten:

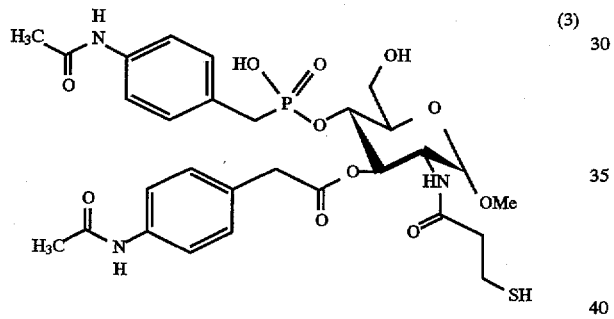

(3)

8. The method of claim 1, wherein the catalytic antibody is produced by hybridoma 17E11 (FERM P-13824).

9. The method of claim 1, wherein the carbohydrate containing the acylated hydroxy group is a gluco-type hexapyranose monosaccharide or an oligosaccharide containing a gluco-type hexapyranose monosaccharide at a non-reducing end.

10. The method of claim 9, wherein the carbohydrate containing the acylated hydroxy group is a monosaccharide or oligosaccharide having the following formula:

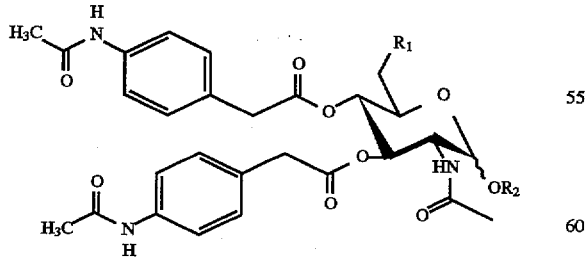

wherein R1 is H, OH, F, OCH$_3$, monosaccharide, oligosaccharide or a group of the formula:

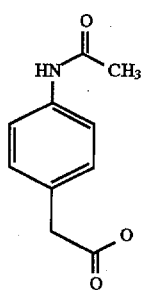

and R$_2$ is H, CH$_3$, monosaccharide or oligosaccharide.

11. The method of claim 9, wherein the carbohydrate containing the acylated hydroxy group is a monosaccharide or oligosaccharide having the following formula:

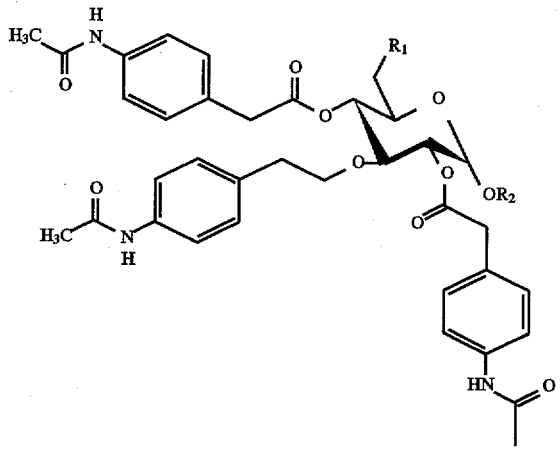

wherein R1 is H, OH, F, OCH$_3$, monosaccharide, oligosaccharides or a group of the formula:

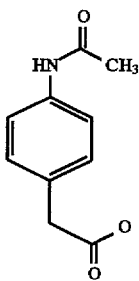

and R$_2$ is H, CH$_3$, monosaccharide or oligosaccharide.

12. A catalytic antibody produced by immunizing an animal with a compound of the following formula:

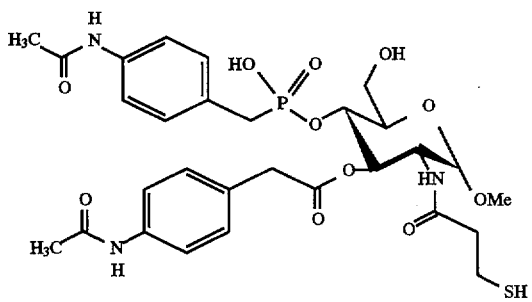

(3)

as a hapten.

13. The antibody of claim 12, which specifically hydrolyzes an acylated hydroxy group of a carbohydrate in a regioselective and stereoselective manner.

14. The antibody of claim 12, which specifically hydrolyzes a 4-acyl group of a carbohydrate in a regioselective and stereoselective manner.

15. The antibody of claim 12, which is produced by hybridoma 17E11 (FERM P-13824).

16. A hybridoma 17E11 (FERM P-13824).

17. A method for producing an oligosaccharide, which comprises the steps of:

(a) preparing a protected carbohydrate comprising a monosaccharide or an oligosaccharide by acylation of all hydroxy groups in the monosaccharide or oligosaccharide with a carboxyl compound, (b) admixing a catalytically effective amount of a catalytic antibody with the monosaccharide or oligosaccharide, wherein the catalytic antibody specifically hydrolyzes a single acylated hydroxy group in the monosaccharide or a single acylated hydroxy group at a non-reducing end of the oligosaccharide in a regioselective and stereoselective manner, thereby deacylating the single acylated hydroxy group in the monosaccharide or oligosaccharide in a regioselective and stereoselective manner, and (c) covalently bonding another monosaccharide or oligosaccharide to the deacylated hydroxy group of the monosaccharide or oligosaccharide obtained in step (b), said catalytic antibody being produced by immunizing an animal using a compound, as a hapten, which is thought to be a transition state analog of desired hydrolysis of the carbohydrate containing the acylated hydroxy group.

* * * * *